United States Patent

Bexelius et al.

[11] Patent Number: 5,717,210
[45] Date of Patent: Feb. 10, 1998

[54] MEASURING DEVICE

[76] Inventors: Per Bexelius, Angsgatan 3 S-661 42; Andreas Todor, Mångatan 24 S-661 33, both of Säffle, Sweden

[21] Appl. No.: 646,327
[22] PCT Filed: Nov. 15, 1994
[86] PCT No.: PCT/SE94/01073
  § 371 Date: Jun. 4, 1996
  § 102(e) Date: Jun. 4, 1996
[87] PCT Pub. No.: WO95/15488
  PCT Pub. Date: Jun. 8, 1995

[30] Foreign Application Priority Data

Dec. 3, 1993 [SE] Sweden ............... 9304021

[51] Int. Cl.$^6$ ............... G01N 21/01; G01N 21/49; G01N 21/85
[52] U.S. Cl. ............... 250/341.2; 250/339.11; 250/341.8
[58] Field of Search ............... 250/339.11, 339.12, 250/341.1, 341.2, 341.8

[56] References Cited

FOREIGN PATENT DOCUMENTS

| 0472899 | 3/1992 | European Pat. Off. |
| 382116 | 1/1976 | Sweden. |
| 453015 | 1/1988 | Sweden. |
| 8203688 | 10/1982 | WIPO. |
| 8302326 | 7/1983 | WIPO. |
| 8809920 | 12/1988 | WIPO ............... 250/339.12 |
| 9315389 | 8/1993 | WIPO. |

*Primary Examiner*—Edward J. Glick
*Attorney, Agent, or Firm*—Michael D. Bednarek; Kilpatrick Stockton LLP

[57] ABSTRACT

A device for measuring the mass of solids contained in a fluid with light. The device includes at least two pairs of light transmitters arranged crosswise. The light transmitters in each pair are able to, at the same time, transmit pulses of light with a certain wavelength, where the wavelengths of the pairs of transmitters are different from each other. The device further includes at least one detector that is able to detect light pulses reflected from the solids as a result of the transmitted light pulses. The detected light pulses are processed to obtain a measurement of the mass of the solids contained in the fluid.

13 Claims, 3 Drawing Sheets

MEASURING DEVICE

TECHNICAL FIELD

The present invention relates to a measuring device for measuring the amount of solids contained in a liquid.

BACKGROUND OF THE INVENTION

There is a need in many processes to know the amount of solids contained in a liquid. In some instances, very small quantities of particles contained in a liquid, i.e. concentrations of a few p.p.m., must be measured, such as in water treatment plants for controlling the purity of drinking water. In other instances, the concentration of fibers suspended in water used in paper mills must be measured to control the various stages during the paper making process. In other industries, such as the food industry there is an interest in measuring the moisture content in food products.

It is known in the art to use photometrical measuring devices by using pulsating light, most often infrared (IR) light, to measure the concentration of particles in liquids. For example, the Swedish Patents Nos. SE-B-382 116, SE-B453 015 and European Patent No. EP-A-96 696 disclose such devices. However, the drawbacks of the earlier devices are many.

When a light beam is passed through a material, the optical radiation is attenuated according to the following formula:

$$P = P_0 e^{-\mu(\lambda) l}$$

where $P_0$ is the initial power of a beam, P is the corresponding power when the beam has travelled a distance 1, or, when used for measurement of concentration, the concentration of particles, and $\mu(\lambda)$ is the attenuation coefficient. The attenuation coefficient is composed of two components: the absorption coefficient $\lambda$ and the scattering coefficient s so that $\mu = \lambda + s$. Of these two components, $\lambda$ is very dependent on the wavelength. Thus, the choice of wavelength is important and therefor infrared fight is chosen for which the absorption is low.

This is important according to the known transmission techniques, because the light transmitted through a suspension is measured, and the difference between the emitted and detected light is a measure of the concentration of solids in the liquid. Too much light must not then be absorbed, leading to low measurement signals.

However, problems with the known technologies stiff remain, because the transmitted energy detected depends exponentially on the concentration according to the formula above so that the detected energy is drastically reduced for higher concentrations of solids. In order to obtain reasonable measurement value signals, it is necessary to use high energies and to transmit short pulses at long intervals in order not to overload the IR-diodes.

The exponential relation also provides further problems such as a need for post treatment of the signals detected to obtain signals that vary according to a linear relationship.

The transmission technology and the exponentially decreasing energy values detected in relation to the concentration of solids implies that the measuring device often cannot be used directly in the process because the distance between transmitter/detector and/or the concentration would be so large that no light could be transmitted. This is solved, as described in Swedish Patent No. 453,015, by diverting a portion of the current and forcing this through a pipe with a defined diameter and with the transmitter/detector positioned opposite each other to provide a "two-dimensional measurement." This requires extensive pipeline constructions for diverting a portion of the current to be measured.

Drawbacks in the form of signals that are not related to the concentration, such as reflection disturbances, temperature dependence of the IR-diodes for the exchange of light, deposits on the sensors and so forth i.e. noise, are difficult to compensate for with the known two-dimensional transmission technologies. In Swedish Patent No. 453,015, a reference device is disclosed that consists of a measuring reference unit in heat transmitting contact with a liquid feeding pipe, wherein the unit is devised to compensate for the temperature dependency of the IR-diodes and the remaining components in the system as well as for any incoming scattered light. These reference units do not measure through the liquid but along a path free of obstacles within the enclosure of the device.

Patent No. EP-A-96 696 describes a device for direct measurement of the moisture content in a specific material by measuring the reflection of IR-radiation from the material instead of using transmission measurement to detect reflections. Interference filters are placed in front of the sensors to separate the relevant wavelengths to be analyzed, and which are dependent upon the material to be measured. Also in this patent, an adjustment device is disclosed to compensate for the temperature dependency of the IR-diodes.

The apparent drawbacks of the conventional technologies result in limitations in the measuring range so that the state of the art measuring devices only measure within a relatively narrow measuring range for which they are specifically designed. Despite the availability of sophisticated electronics, the need for better light emitters and receivers and reference devices still remain a fundamental problem of using the conventional technologies.

BRIEF SUMMARY OF THE INVENTION

The present invention aims at using the advantages of pulsed light when measuring the amount of solid concentration in liquids while removing the existing drawbacks of the prior art.

When an irradiancy, i.e. the radiation from a light source, including infra-red and ultra-violet, hits a solid contained in a liquid, some energy is absorbed. The mount of energy absorbed is determined by the absorption coefficient and is dependent on the wavelength as described above. This absorption pro, ides a spectral displacement towards longer wavelengths on the spectral scale so that wavelengths with higher frequencies are displaced more on the spectral scale than wavelengths with lower frequencies. Thus, the radiance reflected from a solid that is detected by the detector is displaced spectrally as compared to incident radiance.

If two or more pulses of light with different selective wavelengths are emitted, spectral displacements are obtained and the difference between these provide so called spectral contrasts. The proportional change caused by the spectral displacement can be used to obtain a measurement value of the concentration. The mount of displacement is different for different wavelengths and the contrast is a direct function of the mass. When the mass is changed, the contrast will change in direct proportion to the change of the mass.

A measuring probe is provided with, for example, four transmitters, one in each arm of a cross. The transmitters are positioned at the stone distance from the center of the cross and preferably with the same pitch. Oppositely positioned transmitters are interconnected so that they simultaneously transmit a pulse of light in the form of a radiation lobe having a specific wavelength for each of the pairs of transmitters (in this disclosure labelled $\lambda_x$ and $\lambda_y$, respectively), wherein one of the wavelengths is used as a reference. In this way, the particles are illuminated at two wavelengths and with a certain rotational angle in relation to each other. Subsequent pulses are emitted from the two pairs at very short time intervals. A "three-dimensional" illumination of the particles is obtained from this cross, (here labelled λ-cross). However, the probe can be provided with more pairs of oppositely positioned transmitters which transmit at different wavelengths to obtain more information about the media to be measured, such as the amount of particles below a certain size etc. One of the wavelengths used constitutes a reference as described above. However, the configuration of the λ-cross is maintained so that the transmitters are positioned on additional arms of the cross at the same distance from the center of the cross and preferably at the same angle.

One detector is preferably positioned at the center of the cross for detection of the light reflected from the particles at two or more wavelengths.

The contrast hereby created due to the spectral difference between the typically selected wavelengths forms an output signal that is a function of irradiation and the pulse ratio (the contrast) $\lambda_x - \lambda_y$ (or transmitter value minus reference value). The measurement value is the sum/integral of the total contrast detected by the detector. This measurement value contains the spectral difference between the two wavelengths including irrelevant signals, i.e. noise.

However, because the noise is connected to the two pulse answers and is independent from the wavelengths, i.e. the noise is the same for the two pulse answers, this noise can easily be removed by means of a differentiator, and the remainder is the spectral contrast that is a direct function of the mass. Thus, the measuring device does not require any extra reference or compensation devices. Moreover, the detector signal is linear after being filtered.

An important advantage of the proposed method is that the output signal detected by the detector is already digitalized at the measuring point resulting in technical advantages from a measuring point of view.

This measuring method provides much more reliable measurements because all irrelevant signals and disturbances can easily be sorted out by filtering, but above all, the measuring range can be substantially broadened and is in principal only limited by whether the measuring probe can be entered into the media to be measured.

BRIEF DESCRIPTION OF THE DRAWINGS

The measuring device according to the present invention is described in detail below and in connection with a preferred embodiment shown in the attached drawings, wherein.

DETAILED DESCRIPTION

Figure 1:
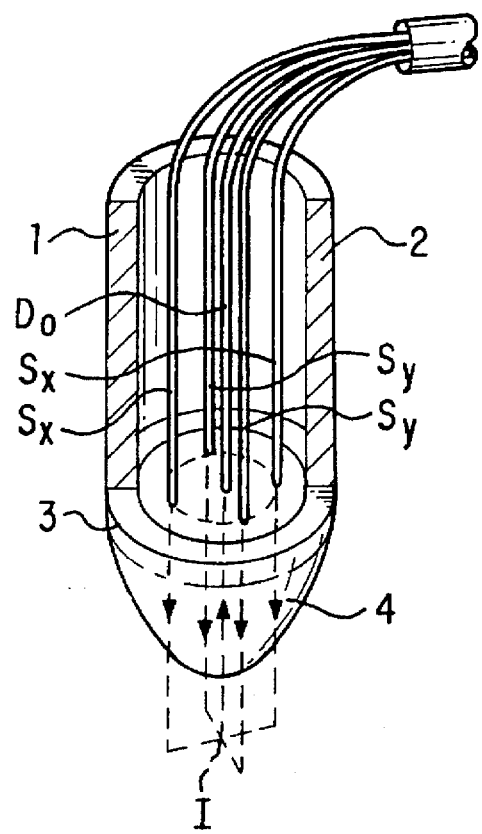
FIG. 1 is a perspective view of a probe according to the preferred embodiment of the present invention.

A measuring device of a preferred embodiment of the present invention, as shown in FIG. 1, includes a probe 1 having a tubular protective enclosure 2. A refractor 3 is mounted at one end of protective enclosure 2. The refractor is for example made of PTFE (poly tetra fluoro ethylene). Mounted on refractor 3 is a body 4 made of glass, PTFE or any other light permeable material. The body may have the shape of being pointed, rounded, aspherical or drop-like, in order not to cause turbulence around the end of the probe, and to decrease its flow resistance. The refraction index between body 4 and water is nearly zero so that very little light from body 4 is reflected and generally will illuminate particles straight in front of probe 1.

Figure 2:
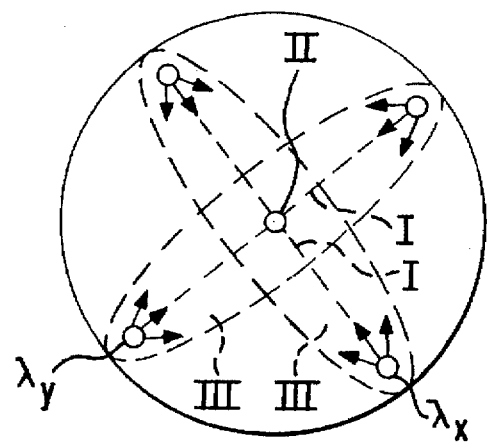
FIG. 2 shows the so called λ-cross with two pairs of sensors and the so called radiation lobes created by the light pulses from the transmitters.

In the preferred embodiment, five optical fiber conductors are used, four for the transmitters ($S_x$, $S_y$) and one for the detector ($D_O$), are drawn in parallel and encapsulated in the protective enclosure 1. The optical fiber conductors are drawn through enclosure 2 and terminate in a layer formed between refractor 3 and body 4. For simplicity, because the transmitters and their optical fiber conductors, respectively, form a unit, they have the same reference in the figures. As seen in FIGS. 1–2, the conductors for the transmitters ($S_x$, $S_y$) and detector $D_O$ are positioned in relation to each other so that they form a cross as seen from beneath probe 1 having the conductor for sensor (D) placed at the point of the intersection of the cross.

The opposite ends of transmitters ($S_x$, $S_y$) are connected to four light-emitting diodes. The light-emitting diodes are chosen and triggered in such a way that the diodes connected to $S_x$, $S_y$ transmitters emit with the same wavelength at the same time, respectively. The wavelengths are selected to be within the wavelengths of infrared and ultraviolet light, i.e. the light-emitting diodes emit light in pairs in two "planes." For example, the light emitting diodes that are connected to $S_x$ may operate at a specific wavelength that is different from the light emitting diodes connected to $S_y$ transmitter and rotated 90 degrees in relation thereto. However, other angular relationships may also be used. FIG. 2 shows how the pulses from each of the pairs form a radiation lobe in order to illuminate the particles located in front of probe 1. The light-emitting diodes are connected to a pulse generator of a known type and triggered so that the two pairs of diodes alternately emit pulses of light at short intervals.

The operation is as follows. A clock frequency with which all the electronics of the measuring device work triggers diodes $S_x$ via the pulse generator so that the diodes emit a light pulse via the two optical fiber conductors $S_x$, in the order of 50–100 μs at the wavelength $\mu_x$. The light pulse illuminates the solids in the liquid that are positioned in front of the probe at this wavelength A very short moment thereafter, the diodes $S_y$ are triggered so that they emit a light pulse at the wavelength $\lambda_y (\neq \lambda_x)$ via the two optical fiber conductors $S_y$ so that the solids positioned in front of the probe are illuminated at this wavelength. The particles in the liquid will thus be illuminated with short subsequent light pulses at two different wavelengths and rotated preferably 90 degrees, a type of cross-modulation.

Figure 4:
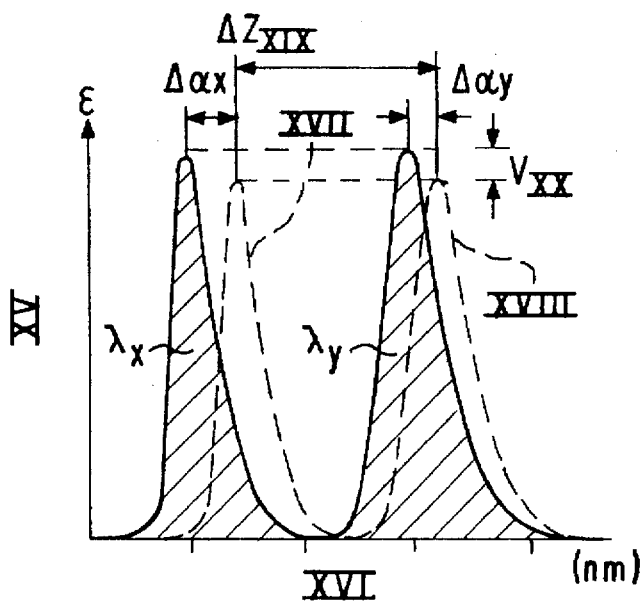
FIG. 4 shows the origin of the spectral contrast during the transmission of two different wavelengths.

FIG. 4 shows the spectral contrast which thus arises due to the spectral difference between the two typically chosen wavelengths when the wavelength $\lambda_x$, having a higher frequency, is shifted more on the spectral scale than $\lambda_y$, having a lower frequency. The sum of the spectral contrast is the difference between the shilling of the two wavelengths which may be described as follows so that $\lambda_z = \Delta\lambda_x - \Delta\lambda_y$.

Figure 3:
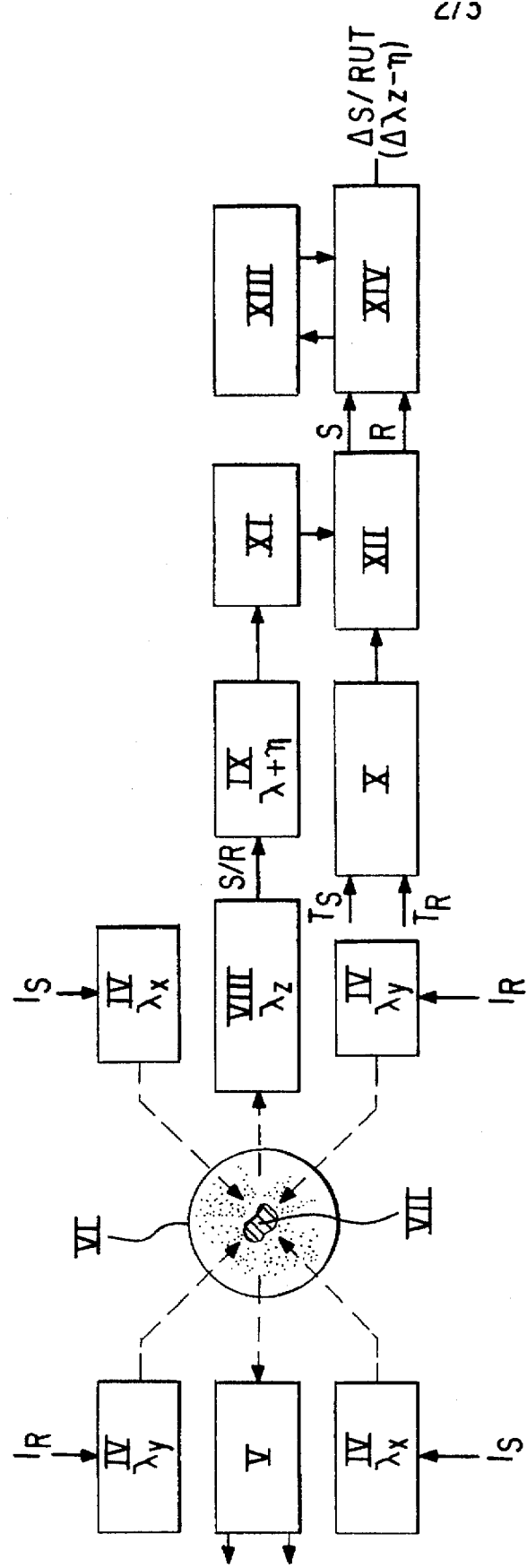
FIG. 3 shows the system of the measuring device and the pulse generator and the decoder/differentiator synchronized by the pulse generator.

Detector $D_O$, which preferably is positioned in the middle of the λ-cross, registers this difference or contrast. The measurement value is the sum of the total contrast registered by the detector. Included in this measurement value is the spectral difference between the two wavelengths including irrelevant signals, i.e. noise. However, because the noise is connected to both of the pulse answers, and this is independent from the wavelengths, i.e. the same for both of the pulse-answers, the noise can be eliminated from the detector signal by means of the arrangement shown in FIG. 3 illustrating a decoder and differentiator of a known type in synchronization with the emitting pulses so that only the spectral contrast remains. This remaining spectral contrast is proportional to the mass of the solids contained in the liquid measured. In this way, samples of signals are obtained by the sequences of incoming pulses of spectral contrasts.

Figure 5A:
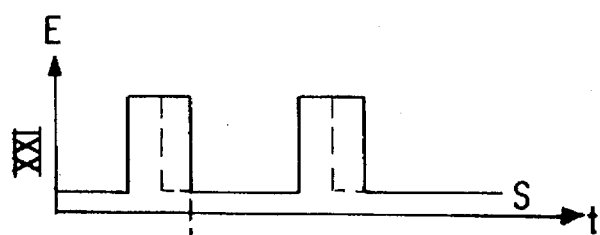
FIG. 5 shows the time relation between the pulses and the responses to the transmitted pulses.
Figure 5B:
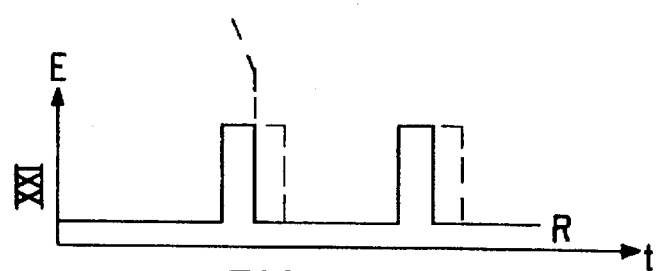
Figure 5C:
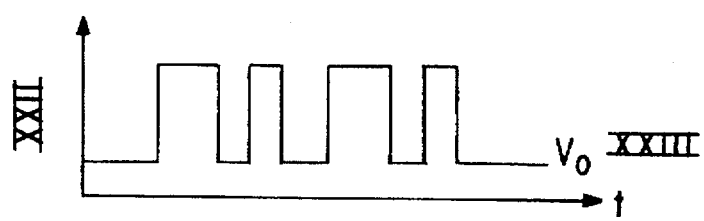

FIG. 5 shows a mutual time-dependency of pulses in graphical depictions for the two transmittor pairs and the responses from the detector as a result of the light reflected from the solids in the liquid. A certain compensation of luminance and chroma can be achieved by extending one of the light pulses in time and shorten the other correspondingly.

The measuring system of the present invention is not limited to only two pairs of transmitters and two wavelengths, but can be expanded with more pairs of emitters transmitting at specific wavelengths which are different from the wavelengths transmitted by other transmitters. For instance, the amount of solids that are smaller than a certain size may be measured by analyzing the spectral contrasts. The measuring system also has the advantage that it covers a large measuring range from a few parts per million up to measuring of moisture content with the same device, which substantially increases the areas of measuring and application in contrast to the prior art devices which all work within a certain measuring range and for a specific application. The measuring principle also has the advantage that the signal detected by the detector is directly distal, providing great measurement-technical advantages and that the output-signal after filtering is linear.

It is to be understood from the above that the measuring system described is not limited to liquids but could also be applied to other media.

It is clear that the invention must not be regarded as limited to the above description and the preferred embodiment shown in the drawings, but can be subjected to different modifications within what is defined in the appending claims.

REFERENCES TO THE DRAWINGS

I λ-Cross
II Receiver
III Radiation lobes
IV Infra-red
V Infra-red modulator
VI Measuring cell
VII -Object,-Contrast,-Noise
VIII Photo detector
IX Amplifier
X System synchronization
XI Detector
XII S/R Data demodulator
XIII Digital filter
XIV Differentiator
XV Relative spectral emission in relation to the wavelength
XVI Wavelength
XVII Sensor phase
XVIII Reference phase
XIX Absorption
XX Loss
XXI Irradiance
XXII Absorption
XXIII Modulator

We claim:

1. A device for measuring the mass of solids contained in a fluid with light, comprising:
   at least two pairs of light transmitters arranged crosswise,
   means for enabling the light transmitters in each pair to, at the same time, transmit pulses of light with a certain wavelength, where the wavelengths of the pairs of transmitters are different from each other,
   at least one detector capable of detecting light pulses reflected from the solids as a result of the transmitted light pulses, and
   means for processing the detected light pulses and obtaining a measurement of the mass of the solids contained in the fluid.

2. The device of claim 1 wherein the wavelengths of the light transmitted are selected within a wavelength range including infrared and ultraviolet.

3. The device of claim 1, wherein the means for enabling the light transmitters further enables the pulses from each pair of light transmitters to be transmitted at regular time intervals, forming pulse trains, and that the pulse trains from the pairs of light transmitters are displaced in time with each other.

4. The device of any of the preceding claims, wherein each light transmitter comprises a light source and an optical fiber conductor.

5. The device of claim 4, wherein a straight line interconnecting ends of the optical fiber conductors in one pair of the light transmitters and a straight line interconnecting ends of the optical fiber conductors in at least another pair of light transmitters form a cross (λ-cross), in which the straight lines intersect with defined angles.

6. The device of claim 5, wherein the angles with which the lines intersect in said λ-cross are equal.

7. The device of claim 5, wherein the detector is positioned in the point of intersection of said λ-cross.

8. The device of claim 4, further comprising a probe, wherein the optical fiber conductors within at least an end portion of said probe are running parallel with each other, said probe adapted to be placed in the fluid of which the mass of solids is to be measured.

9. The device of claim 8, wherein the optical fiber conductors belonging to respective pairs of light transmitters within said end portion form planes, which planes intersect with said defined angles and coincide with said λ-cross.

10. The device of claim 8, wherein said end portion of the probe consists of a refractor.

11. The device of claim 8, wherein ends of the optical fiber conductors in said probe form a plane and that the ends are covered by a light permeable body.

12. The device of claim 11, wherein said body is pointed, rounded, aspherical or drop-shaped in order to reduce the flow resistance of the probe.

13. The device of claim 8, wherein the detector also comprises an optical fiber conductor, and that an end of said optical fiber conductor of said detector is in the same plane in the probe as the ends of the optical fiber conductors of the light transmitters.

* * * * *